United States Patent

Berg

[11] Patent Number: 6,042,697

[45] Date of Patent: Mar. 28, 2000

[54] SEPARATION OF 9,11-DIENE C18 FATTY ACID FROM 10,12-DIENE C18 FATTY ACID BY AZEOTROPIC DISTILLATION

[76] Inventor: Lloyd Berg, 1314 S. 3rd Ave., Bozeman, Mont. 59715

[21] Appl. No.: 09/363,882

[22] Filed: Jul. 30, 1999

[51] Int. Cl.[7] ............................... B01D 3/36; C07C 51/46
[52] U.S. Cl. .................. 203/57; 203/60; 203/62; 203/63; 203/64; 203/68; 203/69; 203/70; 554/175; 554/185; 554/206; 554/210; 554/212; 554/184
[58] Field of Search .................. 203/57, 60, 62, 203/68, 70, 69, 63, 64; 554/1, 175, 185, 180, 184, 199, 206, 210, 212

[56] References Cited

U.S. PATENT DOCUMENTS

| | | | |
|---|---|---|---|
| 3,737,444 | 6/1973 | Hartmann et al. | 554/187 |
| 3,804,819 | 4/1974 | Wengrow et al. | 554/188 |
| 4,345,976 | 8/1982 | Peter et al. | 203/68 |

*Primary Examiner*—Virginia Manoharan

[57] ABSTRACT

9,11- Diene C18 fatty acid cannot be separated from 10,12-Diene C18 fatty acid by conventional rectification because of the proximity of their boiling points. 9,11-Diene C18 fatty acid can be readily separated from 10,12-Diene fatty acid by azeotropic distillation. Effective agents are propyl formate, butyl ether, methyl pivalate and cyclopentanone.

2 Claims, No Drawings

SEPARATION OF 9,11-DIENE C18 FATTY ACID FROM 10,12-DIENE C18 FATTY ACID BY AZEOTROPIC DISTILLATION

FIELD OF THE INVENTION

This invention relates to a method for separating 9,11-diene C18 fatty acid from 10,12-diene C18 fatty acid by azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual method of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

9,11-Diene C18 Fatty Acid and 10,12-Diene C18 Fatty Acid boil only about a degree apart, have a relative volatility of 1.05 and are impossible to separate by conventional rectification. Table 2 shows that with an agent giving a relative volatility of 1.85 only 20 actual plates are required,

TABLE 2

Theoretical and Actual Plates Required vs. Relative Volatility for 9,11-Diene C18 Fatty Acid vs. 10,12-Diene C18 Fatty Acid

| Relative Volatilty | Theoretical Plates Required At Total Reflux, 99% Purity | Actual Plates Required, 75% Eff. |
|---|---|---|
| 1.65 | 19 | 26 |
| 1.75 | 16 | 22 |
| 1.85 | 15 | 20 |

OBJECTIVE OF THE INVENTION

The objects of this invention are to provide a process for the separation of 9,11-Diene C18 fatty acid from 10,12-Diene C18 fatty acid which entails the use of certain organic compounds when employed as the agent in azeotropic distillation.

DETAILED DESCRIPTION OF THE INVENTION

I have discovered that certain organic compounds will effectively increase the relative volatility between 9,11-Diene C18 fatty and 10,12-Diene C18 fatty acid during rectification when employed as agent in azeotropic distillation. They are isopropyl acetate, 3-methyl-2-butanone, nitroethane, 2-nitropropane,N,N-dimethylformamide, amyl acetate, ethyl acetoacetate, 1-decene, propyl formate, butyl ether, butyraldehyde, ethylene glycol dimethyl ether, methyl pivalate, hexyl formate, cyclopentanone and nonane.

TABLE 3

Effective Azeotropic Distillation Agents For Separating 9,11-Diene C18 Fatty Acid From 10,12-Diene C18 Fatty Acid

| Compounds | Relative Volatility |
|---|---|
| None | 1.1 |
| Isopropyl acetate | 1.2 |
| 3-Methyl-2-butanone | 1.45 |
| Nitroethane | 1.25 |
| 2-Nitropropane | 1.25 |
| N,N-Dimethylformamide | 1.55 |
| Amyl acetate | 1.55 |
| Ethyl acetoacetate | 1.4 |
| 1-Decene | 1.65 |
| Propyl formate | 1.75 |
| Butyl ether | 1.25 |
| Butyraldehyde | 1.35 |
| Ethylene glycol dimethyl ether | 1.3 |
| Methyl pivalate | 1.45 |

TABLE 4

Effective Azeotropic Distillation Agents For Separating 10,12-Diene C18 Fatty Acid From 9,11-Diene C18 Fatty Acid

| Compounds | Relative Volatility |
|---|---|
| None | 1.1 |
| Hexyl formate | 1.5 |
| Cyclopentanone | 1.85 |
| Nonane | 1.25 |

THE USEFULNESS OF THE INVENTION

The usefulness or utility of this invention can be demonstrated by referring to the data presented in Tables 1, 2, 3 and 4. All of the successful agents show that 9,11-Diene C18 fatty acid can be separated from 10,12-Diene C18 fatty acid by means of azeotropic distillation and that the ease of separation is considerable.

WORKING EXAMPLES

Example 1

Fifty grams of 9,11-Diene C18 fatty acid—10,12-Diene-C18 fatty acid mixture and fifty grams of propyl formate as the azeotrope forming agent were charged to a vapor—liquid equilibrium still and refluxed for two hours. The vapor composition was 55% 9,11-Diene C18 fatty acid, 45% 10,12-Diene C18 fatty acid; the liquid composition was 41% 9,11-Diene C18 fatty acid, 59% 10,12-Diene C15 fatty acid, Thie is a relative volatility of 1.75.

Example 2

Fifty grams of 10,12-Diene C18 fatty acid—9,11-Diene-C18 fatty acid mixture and fifty grams of cyclopentanone as the azeotrope forming agent were charged to vapor—liquid equilibrium still and refluxed for two hours. The vapor composition was 77% 10,12-Diene C18 fatty acid, 23% 9,11-Diene C18 fatty acid, the liquid composition was 64.5% 10,12-Diene C18 fatty acid, 35.5% 9,11-Diene-C18 fatty acid. This is a relative volatility of 1.85.

I claim:

1. A method for recovering 9,11-Diene C18 fatty acid from a mixture of 9,11-Diene C18 fatty acid and 10,12-Diene C18 fatty acid which comprises distilling a mixture of 9,11-Diene C18 fatty acid and 10,12-Diene C18 fatty in the presence of an azeotrope forming agent, recovering the 9,11-Diene C18 fatty acid and the azeotrope forming agent as overhead product and obtaining the 10,12-Diene C18 fatty acid as bottoms product, wherein said azeotrope forming agent consists essentially of one material selected from the group consisting of 3-methyl-2-butanone, nitroethane, 2-nitropropane, N,N-dimethylformamide, amyl acetate, ethyl acetoacetate, 1-decene, propyl formate, butyl ether, butyraldehyde, ethylene glycol dimethyl-ether and methyl pivalate.

2. A method for recovering 10,12- Diene C18 fatty acid from a mixture of 10,12-Diene C18 fatty acid and 9,11-Diene C18 fatty acid which comprises distilling a mixture of 10,12-Diene fatty acid and 9,11-Diene C18 fatty acid in the presence of an azeotrope forming agent, recovering the 10,12-Diene C18 fatty acid and the azeotrope forming agent as overhead product as overhead product and obtaining the 9,11 -Diene C18 fatty acid as bottoms product, wherein said azeotrope forming agent consists essentially of one material selected from the group consisting of hexyl formate and cyclopentanone.

* * * * *